United States Patent [19]

Arlers et al.

[11] 4,216,771
[45] Aug. 12, 1980

[54] HYPODERMIC SYRINGE WITH ASPIRATION EFFECT

[76] Inventors: Sven Arlers, Göteborgsväen 77; LGunnar Nilsson, Blankavägen 46, both of Partille, Sweden, 433 00

[21] Appl. No.: 857,619

[22] Filed: Dec. 5, 1977

[30] Foreign Application Priority Data

Dec. 14, 1976 [SE] Sweden ............................ 7611663
Feb. 23, 1977 [SE] Sweden ............................ 7701971

[51] Int. Cl.² ........................................... A61M 5/00
[52] U.S. Cl. ................................. 128/218 P; 128/234
[58] Field of Search ........ 128/218 PA, 218 D, 218 R, 128/218 P, 218 F, 215, 276, 234

[56] References Cited

U.S. PATENT DOCUMENTS

| | | | |
|---|---|---|---|
| 3,224,445 | 12/1965 | Melott | 128/218 D |
| 3,340,872 | 9/1967 | Cox | 128/218 D |
| 3,583,399 | 6/1971 | Ritsky | 128/218 D |
| 3,797,487 | 3/1974 | Schmidt | 128/218 PA |
| 3,834,387 | 9/1974 | Brown | 128/218 P |

*Primary Examiner*—John D. Yasko
*Attorney, Agent, or Firm*—Holman & Stern

[57] ABSTRACT

A hypodermic syringe is provided with aspiration effect and comprises a cylindrical member or ampoule, a piston, a piston rod and an aspiration rod, which is connected to the piston. The aspiration rod extends through a channel in the piston rod and is at its remote end from the piston provided with or connected to an actuating member. By means of said actuating member the aspiration rod can be displaced in the channel in the piston rod, thereby displacing the piston or a part of the piston relative to the ampoule, thus performing aspiration.

8 Claims, 16 Drawing Figures

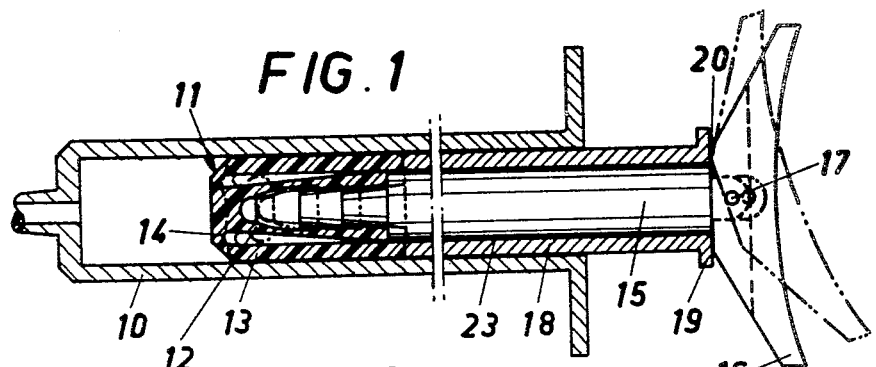
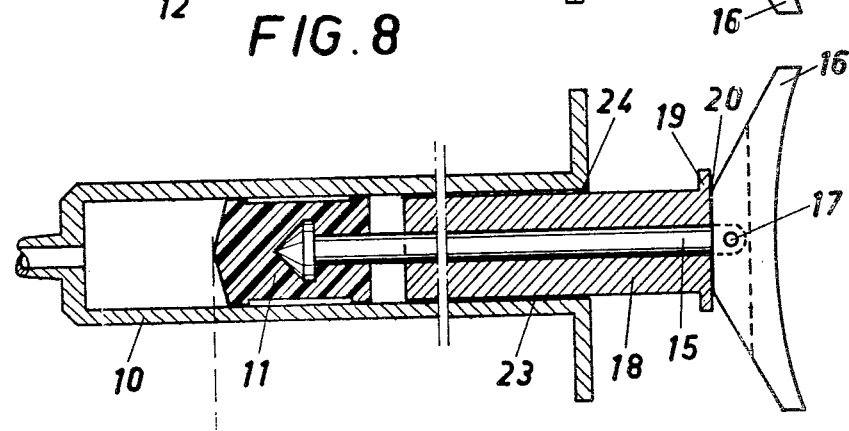
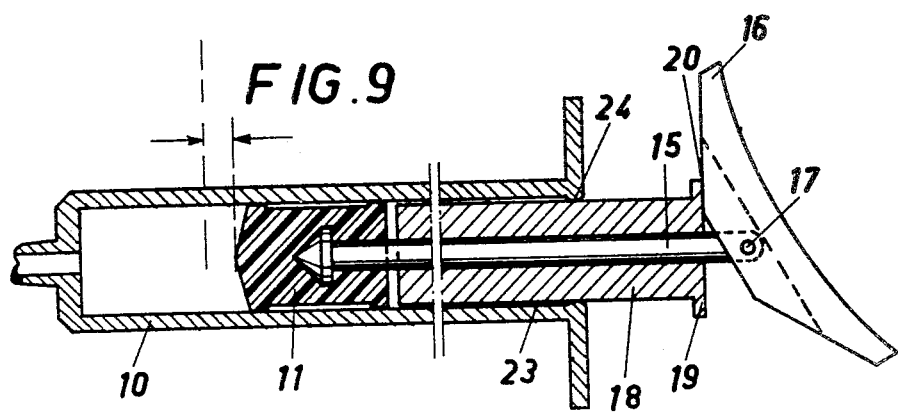

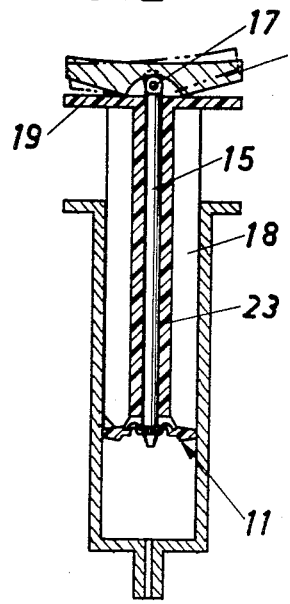
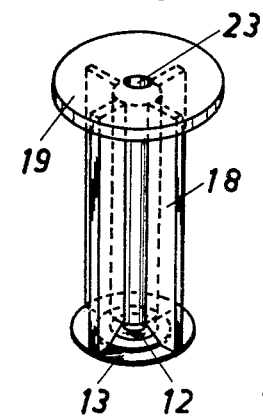
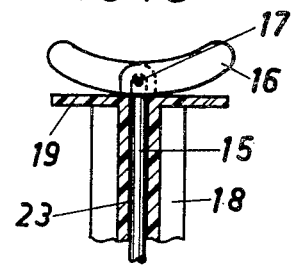
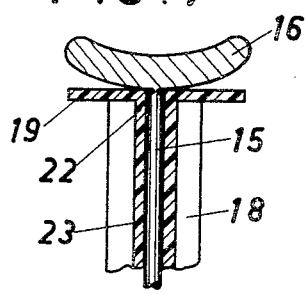
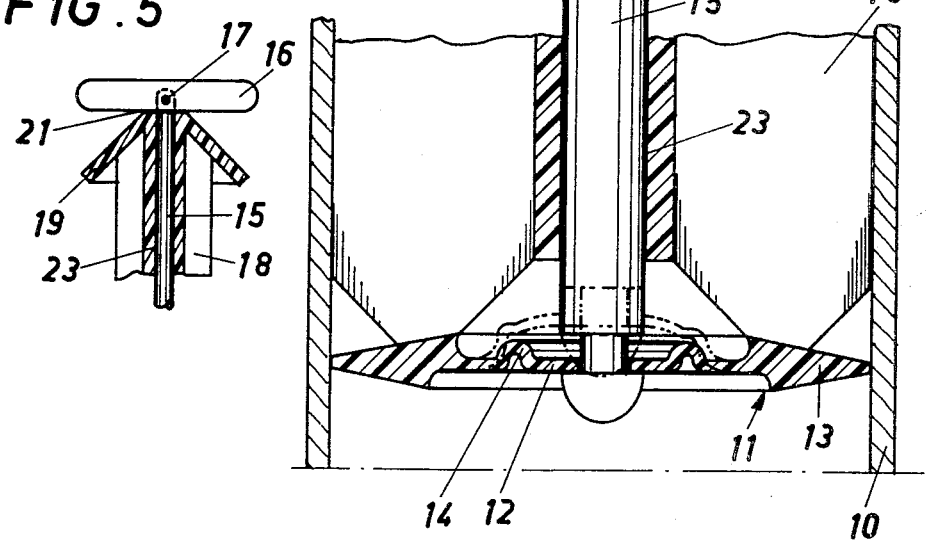

U.S. Patent  Aug. 12, 1980  Sheet 3 of 4  4,216,771
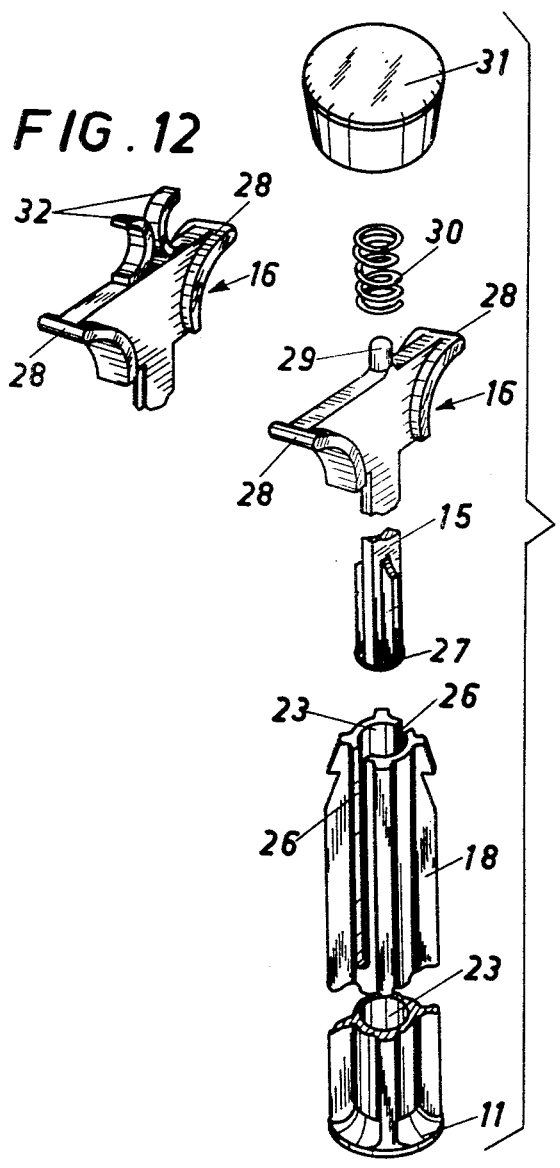
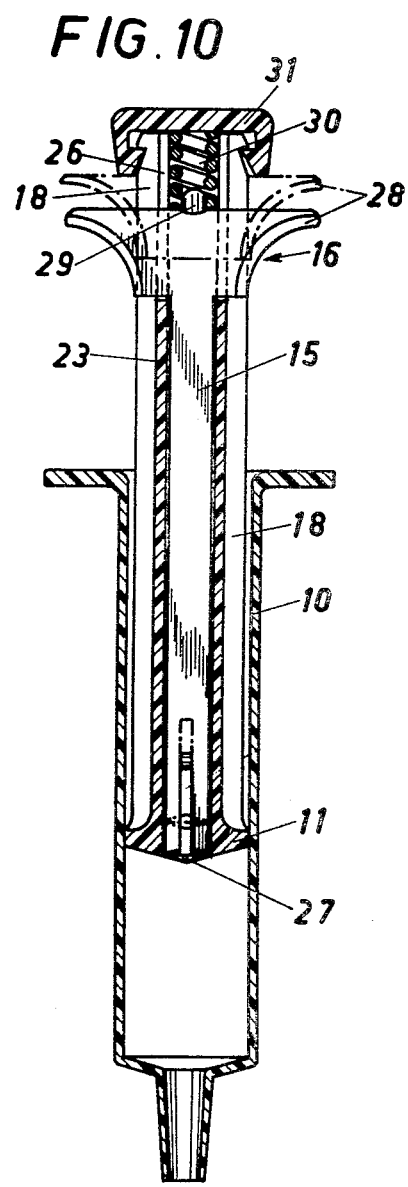

HYPODERMIC SYRINGE WITH ASPIRATION EFFECT

BACKGROUND OF THE INVENTION

The present invention relates to a hypodermic syringe with aspiration effect, comprising a cylindrical member or ampoule, a piston rod and a piston, which is connectable or combined to an aspiration rod and arranged to cooperate with the piston rod.

At odontological local anaesthesia the intention is to locate the anasthetic in the tissue. Intravasal injection, e.g. injection into a vein, should be avoided from medical and practical point of view, as the risk for secondary effects is large and the anasthetic is rapidly washed away from the injection area. It is therefore a requirement that an aspiration shall be made before the injection. Aspiraton should always be accomplished when you want to be sure that the cannula at intravenous injection has punctured a vein or an intramuscular injection has not entered a blood vessel.

For known hypodermic syringes with aspiration effect the piston can be so designed, that a diaphragm is forced to curve inwards in the cylindrical member when a pressure is exerted on the piston rod. A small quantity of fluid is thereby pressed aside and when the pressure on the piston rod is reduced, the diaphragm returns to its original position. Hereby a negative pressure will arise in the cylindrical member and fluid from the injection area may flow into the cylindrical member. The disadvantage of such a hypodermic syringe is that it is difficult and awkward to use, as a pressure has to be applied on the piston rod when the cannula is entered into the tissue. When this pressure is reduced, aspiration will be achieved. Moreover, it is difficult for anyone to determine the quantity of aspiration with such a syringe.

A hypodermic syringe is also known where the aspiration can be achieved without applying any pre-pressure on the actuating member. This hypodermic syringe, however, shows a very complicated and expensive design and it is not appropriate for non-recurrent use. According to another known proposal the standard piston is used also for aspiration, but this embodiment leads to the complication that the friction between the piston and the inner side of the cylinder has to be less than the friction between the piston rod and the inner side of the cylinder, to be able to perform the aspiration. This, however, results in the fact that the double friction at injection may be troublesome.

SUMMARY OF INVENTION

The aim of the present invention is to propose a hypodermic syringe with aspiration effect, where the aspiration is achieved without having to apply any pre-pressure on the actuating member before the cannula has been entered into its position in the tissue. It shall also be possible to control the quantity of aspiration oneself. Moreover, the hypodermic syringe is to be of a simple design and well suitable for manufacture as a disposable article.

According to the invention this has been solved thereby that the aspiration rod is arranged to be guided in a channel extending through the piston rod and that the end of the aspiration rod remote from the piston is located outside the piston rod and provided with or connected to an actuating member designed for axial displacement of the aspiration rod relative to the piston rod.

DESCRIPTION OF DRAWINGS

In the following the invention will be further described with reference to some embodiments shown in the accompanying drawings.

FIG. 1 is a section through an embodiment of the hypodermic syringe according to the invention, FIG. 2 is a section through another embodiment of the hypodermic syringe, FIG. 3 is a perspective view of the piston rod and of the piston fixed to said piston rod according to the embodiment in FIG. 2, FIG. 4 shows a part of FIG. 2 in a larger scale, FIGS. 5, 6 and 7 are sections showing different designs of the actuating member, FIGS. 8 and 9 show sections of a modified embodiment of the invention in two different function positions, FIG. 10 is a section through another embodiment of the hypodermic syringe according to the invention, FIG. 11 is an exploded view of the syringe according to FIG. 10, FIG. 12 shows a modified design of a detail in FIG. 11.

DETAILED DESCRIPTION OF THE EMBODIMENTS

Figure 13:
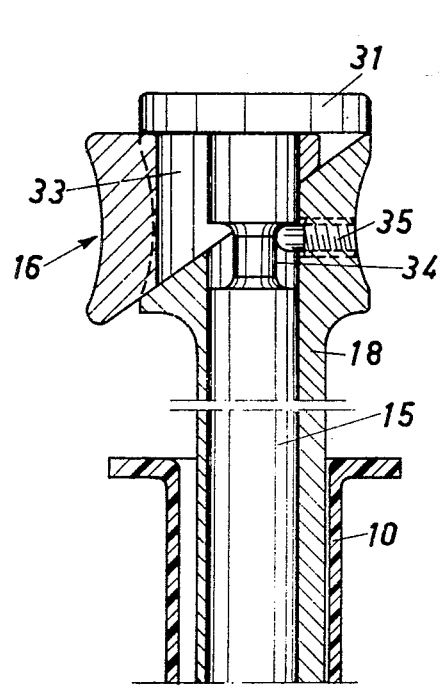
FIG. 13 is a section through a further embodiment of the actuating member showing this in its initial position.

According to the embodiment of FIG. 1 the hypodermic syringe comprises a cylindrical member or ampoula 10 and a piston 11 consisting of two members displaceable relative to each other, i.e. an inner 12 and an outer member 13, which are connected by means of a diaphragm 14. The inner member 12 of the piston 11 is attached to one end of an aspiration rod 15, at the opposite end of which an actuating member 16 is pivotably arranged. The pivot axle consists of a hinge 17 arranged at a part of the aspiration rod 15 projecting outside the cylindrical member 10.

The aspiration rod 15 extends through a piston rod 18 provided with a central through channel 23, which piston rod with one end abuts the piston 11 and with the other end abuts the actuating member 16. The piston rod 18 is provided with a collar or a circumferential flange 19. The actuating member 16 has on its lower side a surface chamfered upwards, so that an edge 20 is formed, around which edge the actuating member 16 can be swung up and down when revolving round the hinge 17.

According to the embodiments in FIGS. 2–7 the piston rod 18 shows a cross section in the form of a cross with a centric channel 23, through which the aspiration rod extends. Such a piston rod is similar to a piston rod for a hypodermic syringe for disposable use that is of frequent use today. By some small modifications it can be designed so that it is well suitable for use as a hypodermic syringe with aspiration effect. The piston rod 18 is at its bottom end fixed to the piston 11, which in this case shows a somewhat modified shape compared to FIG. 1. The piston 11, however, consists also in this case of an inner part 12 and an outer part 13 displaceable relative to each other and connected by the diaphragm 14. The aspiration rod 15 is fixed to the inner part 12 of the piston 11.

In the embodiment according to FIG. 5 the collar 19 of the piston rod 18 is chamfered downwards and it has therefore an edge 21, about which edge the actuating member 16 is pivotable. The lower side of the actuating member 16 may be completely planar.

According to the embodiments in FIGS. 6 and 7 the underside of the actuating member 16 shows a convex form to make possible the pivoting motion.

According to the embodiment in FIG. 7 the aspiration rod 15 and the actuating member 16 are manufactured in one piece, e.g. of plastic, and a portion 22, with essentially reduced material thickness, is arranged between the aspiration rod 15 and the actuating member 16, about which portion 22 the actuating member 16 pivots.

The hypodermic syringe unit, including the piston 11, the piston rod 18, the aspiration rod 15 and the actuating member 16, is when used connected to the cylindrical member or the ampoule 10. Thereafter a cannula (not shown) is fitted to the cylindrical member or ampoule 10. Air which may be enclosed in the cylindrical member 10 is evaquated in the usual manner by a small quantity of the fluid being ejected from the syringe, with its needle pointing upwards.

When performing the aspiration the actuating member 16 is pivoted about the hinge 17 or the portion 22 with the reduced material thickness, whereby the inner part 12 of the piston 11 is drawn upwards so that a subpressure arises in the cylindrical member or ampoule 10, and fluid from the injection area can flow into the cylindrical member. Should the result of the aspiration be negative, pressure is to be applied centrically on the actuating member 16, whereby the piston rod 18 will act upon the piston 11 and an injection occurs. The finger grip round the syringe need not be changed from aspiration to injection, whereby a safety against intravasal injection is achieved, as the position of the cannula is not altered.

The modified embodiment shown in FIGS. 8 and 9 consists, like in previously described examples, of one cylindrical member 10, a piston 11, an aspiration rod 15 and a piston rod 18. This embodiment differs from the one described above thereby that the piston is of conventional type, i.e. it lacks the diaphragm mentioned above and is not divided into two parts. At aspiration the entire piston will thus make an axial displacement and to make this possible a friction element 24 is arranged between the piston rod 18 and the inner side of the cylinder 10; said friction element being disposed at the inner side of the cylinder or at the outer side of the piston rod. In the embodiment shown the inner side of the cylinder is provided with a peripherical boss 24 close to the one open end of the cylinder. The friction between the members 10 and 18 is chosen so that it exceeds the friction between the piston and the inner side of the cylinder, but is not too large to make it possible to inject without difficulties. The aspiration occurs in accordance with the embodiments described above, i.e. the actuating member 16 is pivoted round the pivot axle 17.

A springy element arranged to press the piston back from the aspiration position to the initial injection position, may be arranged in the space between the piston 11 and the piston rod 18. The springy element can be for instance a ring-shaped extension of the plunger, which is made of rubber.

The hypodermic syringe according to the invention can be easily manufactured at a low price as a disposable article, whereby hygienic and practical advantages will be achieved.

The embodiment shown in FIGS. 10 and 11 comprises a cylindrical member or ampoule 10, a piston 11 and a piston rod 18 made in one piece with said piston. An aspiration rod 15 extends through a central axial channel 23 in the piston rod 18, which in its upper end is slit open by slots 26. The bottom part of the aspiration rod 15 is designed as a plunger 27, which sealingly abuts the interior of the channel 23, whereas its upper part is provided with an actuating member 16 designed as wings 28 projecting sideways, said wings being arranged to extend through the slots 26 of the piston rod. In its initial position the plunger 27 is located essentially on a level with the free end of the piston 11, whereas the plunger 27 is by means of actuating member 16 displaced inwards into the channel 23 to perform aspiration.

The actuating member 16 is on its top side provided with a central boss 29, round which a coil spring 30 is arranged. A pressure plate 31 can be snap-locked on the upper end of the piston rod 18 and form a holder-on for the spring 30.

Aspiration can be achieved in that the actuating member 16 by means of the spring 30 is drawn upwards towards the pressure plate 31, whereby the aspiration rod 15 and the plunger 27 are displaced and consequently causes a negative pressure in the cylindrical member or ampoule 10. The injection is performed in the conventional manner by applying pressure onto the pressure plate 31, whereby the piston rod 18 and the piston 11 are displaced downwards into the cylindrical member or ampoule 10.

FIG. 12 shows the actuating member 16 provided with a couple of springy projections 33 on its upper side and a separate spring 30 is thus not required. These springy projections 33 could of course alternatively be arranged on the bottom side of the pressure plate 31.

Figure 14:
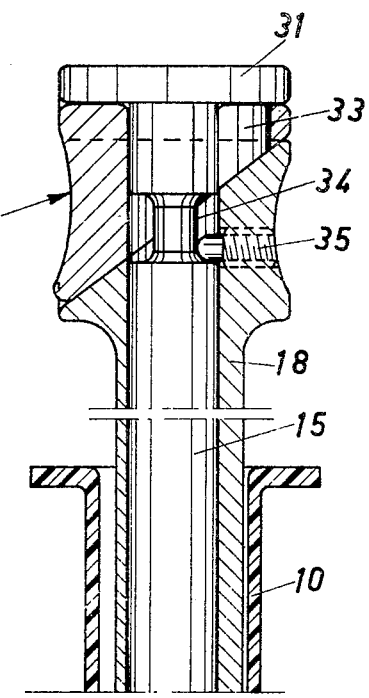
FIG. 14 is a section similar to that of FIG. 13 but showing the actuating member in the aspiration position.

According to the embodiment of FIGS. 13 and 14 the pressure plate 31 is fixed to, i.e., integral with the aspiration rod 15. The actuating member 16 consists of a body with an essentially planar upper side, which engages to the bottom side of the pressure plate 31. The underside of the actuating member 16 shows a sloping or linearly inclined limitation surface, which engages a surface, designed in a similar way, at the upper end of the piston rod 18. The actuating member 16 is provided with a through hole 33 with an oblong section, through which hole the aspiration rod 15 is extending. The aspiration rod 15 has a substantially circular cross-section, whereby the actuating member 16 can perform a radial movement relative to this rod.

In initial position the actuating member 16 takes the position shown in FIG. 13, whereby the part of the actuating member 16 showing the largest height, will project beyond the side of the piston rod 18 and the pressure plate 31. The pressure plate 31 abuts the piston rod 18 and the bottom end of the aspiration rod 15 is located essentially on the same level as the free end of the piston 11. In order to perform aspiration the actuating member 16 is pressed inwards to the position shown in FIG. 14, the pressure plate 31 thereby being influenced, so that said plate together with the aspiration rod 15 will perform a movement upwards. Injection is performed in a usual manner by applying a pressure on the pressure plate 31, whereby the piston rod 15 and the piston 11 are displaced downwards in the cylindrical member 10 and the actuating member 16 is pressed outwards to its initial position.

To prevent the aspiration rod 15 from coming loose from the piston rod 15, the aspiration rod 15 is provided with a neck 34 with reduced cross-sectional diameter and the end of a screw 35 or similar abuts said neck 34. The height of the neck 34 is sufficient to admit necessary movement between the aspiration rod 15 and the piston rod 18 to perform aspiration.

Figure 15:
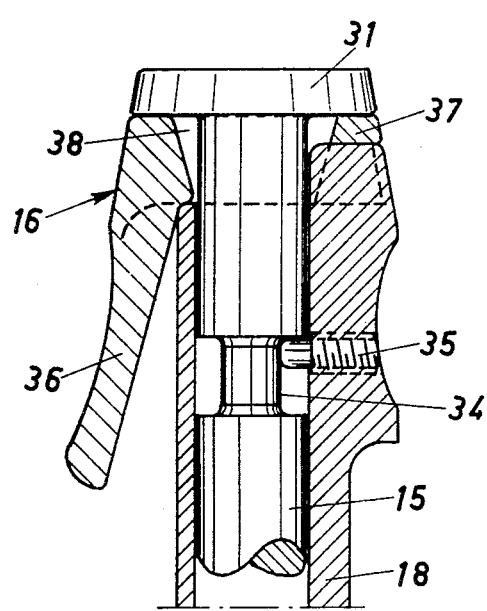
FIG. 15 is a section showing another embodiment of the actuating member in its initial position.
Figure 16:
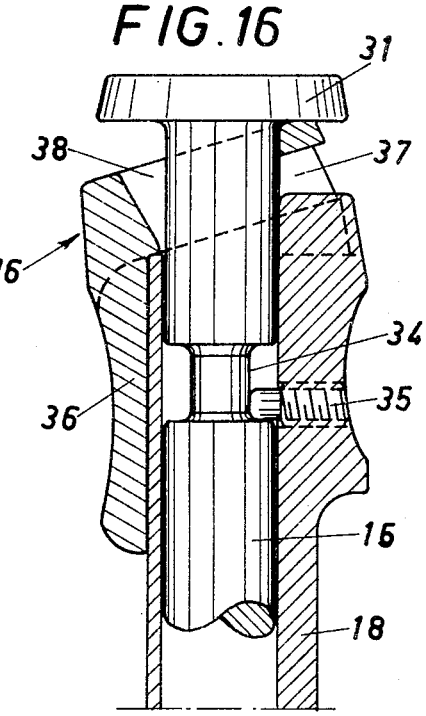
FIG. 16 is a section similar to that of FIG. 15 but showing the actuating member in aspiration position.

According to the embodiment in FIGS. 15 and 16 the actuating member 16 comprises a lever 36 and a portion 37 projecting from the lever 36 at an obtuse angle. Said portion 37 shows a central through opening 38, through which the aspiration rod 15 extends. The opening 38 has an increasing diameter in the upward direction.

In the initial position, that is the position shown in FIG. 15, lever 36 extends somewhat outside the piston rod 18 and the bottom side of the portion 37 contacts a surface at the upper end of the piston rod 15, whereas the pressure plate 31 engages the upper side of the portion 37. As in the embodiment according to FIGS. 13 and 14 the pressure plate 31 is integral with the aspiration rod.

The lever 36 is pressed against the piston rod 18 to the position shown in FIG. 16 to perform aspiration, and the portion 37 makes a pivoting movement pressing the pressure plate 31 together with the aspiration rod 15 upwards.

The invention is of course not limited to the embodiments shown but can be varied within the scope of the following claims.

We claim:

1. An aspiration hypodermic syringe comprising a cylindrical member, a piston and an aspirating member contained within said cylindrical member, a piston rod and an aspiration rod for operating said piston and said aspirating member respectively, said aspiration rod being contained within said piston rod and said piston rod and aspiration rod extending from one end of said cylindrical member, said piston and aspirating member being arranged for limited relative axial movement, said aspirating member having an inner limit of axial movement relative to said piston and an outer limit of axial movement relative to said piston and actuating means at an outer end of said aspiration rod for manually outwardly displacing said aspiration rod relative to said piston rod when said aspirating member is at its inner limit of axial movement relative to said piston to provide an aspirating movement of said aspirating member relative to said piston wherein said actuating means comprises a transverse member pivotally connected at said outer end of said aspiration rod, said transverse member having a camming surface for engaging the outer end of said piston rod and axially moving said aspiration rod relative to said piston rod by rocking movement of said camming surface relative to said outer end of the piston rod.

2. Syringe of claim 1 including pivot means connecting said transverse member to said aspiration rod.

3. The syringe of claim 1 wherein said transverse member is integral with said aspiration rod.

4. An aspirating hypodermic syringe comprising a cylindrical member, a piston and an aspirating member contained within said cylindrical member, a piston rod and an aspiration rod for operating said piston and said aspirating member respectively, said aspiration rod being contained within said piston rod and said piston rod and aspiration rod extending from one end of said cylindrical member, said piston and aspirating member being arranged for limited relative axial movement, said aspirating member having an inner limit of axial movement relative to said piston and an outer limit of axial movement relative to said piston and actuating means at one outer end of said aspiration rod for manually outwardly displacing said aspiration rod relative to said piston rod when said aspirating member is at its inner limit of axial movement relative to said piston to provide an aspirating movement of said aspirating member relative to said piston, the syringe including means defining longitudinal slots in an outer end portion of said piston rod, said actuating means including radial members extending through said slots.

5. The syringe of claim 4 including opposed pressure plate means at the outer ends of said piston rod and said aspiration rod respectfully and spring means interposed between said pressure plate means, said spring means urging said aspiration rod inwardly of said cylindrical member relative to said piston rod.

6. As aspirating hypodermic syringe comprising a cylindrical member, a piston and an aspirating member contained within said cylindrical member, a piston rod and an aspiration rod for operating said piston and said aspirating member respectively, said aspiration rod being contained within said piston rod and said piston rod and aspiration rod extending from one end of said cylindrical member, said piston and aspirating member being arranged for limited relative axial movement, said aspirating member having an inner limit of axial movement relative to said piston and an outer limit of axial movement relative to said piston and actuating means at one outer end of said aspiration rod for manually outwardly displacing said aspiration rod relative to said piston rod when said aspirating member is at its inner limit of axial movement relative to said piston to provide an aspirating movement of said aspirating member relative to said piston,
the syringe including a pressure plate at the outer end of said aspiration rod, means defining an inclined surface at the outer end of said piston rod, and an actuating member between said piston rod and said pressure plate, said actuating member having a further inclined surface conforming to said inclined surface on said piston rod for moving said aspiration rod outwardly relative to said piston rod within a wedge-like action.

7. The syringe of claim 6 wherein said actuating member includes means defining a through-hole receiving the outer end of said aspiration rod.

8. An aspirating hypodermic syringe comprising a cylindrical member, a piston and an aspirating member contained within said cylindrical member, a piston rod and an aspiration rod for operating said piston and said aspirating member respectively, said aspiration rod being contained within said piston rod and said piston rod and aspiration rod extending from one end of said cylindrical member, said piston and aspirating member being arranged for limited relative axial movement, said aspirating member having an inner limit of axial movement relative to said piston and an outer limit of axial movement relative to said piston and actuating means at one outer end of said aspiration rod for manually outwardly displacing said aspiration rod relative to said piston rod when said aspirating member is at its inner limit of axial movement relative to said piston to provide an aspirating movement of said aspirating member relative to said piston wherein said actuating means includes a pressure plate means at the outer end of said actuating rod and a rocking member interposed between said pressure plate means and the outer end of said piston rod for moving said aspiration rod outwardly relative to said piston rod by a camming action, said rocking member including a ring portion encircling a part of said aspiration rod adjacent said pressure plate means and a lever portion connected to said ring portion.

* * * * *

UNITED STATES PATENT AND TRADEMARK OFFICE
CERTIFICATE OF CORRECTION

PATENT NO. : 4,216,771
DATED : August 12, 1980
INVENTOR(S) : Sven Arlers, and Gunnar Nilsson It is certified that error appears in the above-identified patent and that said Letters Patent are hereby corrected as shown below:

[76] Inventors:

"LGunnar" should read --Gunnar--

Signed and Sealed this

Twenty-eighth Day of October 1980

[SEAL]

Attest:

SIDNEY A. DIAMOND

Attesting Officer

Commissioner of Patents and Trademarks